(12) United States Patent
Herzig et al.

(10) Patent No.: US 8,741,979 B2
(45) Date of Patent: Jun. 3, 2014

(54) PROCESS FOR PRODUCING SILOXANE COPOLYMERS WITH URETHANE-SULPHONAMIDO LINKING GROUPS

(75) Inventors: Christian Herzig, Waging (DE); Christine Sivac, Kirchdorf (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 13/812,112

(22) PCT Filed: Jul. 20, 2011

(86) PCT No.: PCT/EP2011/062460
§ 371 (c)(1),
(2), (4) Date: Jan. 24, 2013

(87) PCT Pub. No.: WO2012/013558
PCT Pub. Date: Feb. 2, 2012

(65) Prior Publication Data
US 2013/0123376 A1    May 16, 2013

(30) Foreign Application Priority Data

Jul. 27, 2010 (DE) .......................... 10 2010 038 487

(51) Int. Cl.
    *C07F 7/18*      (2006.01)
    *G03F 7/029*      (2006.01)

(52) U.S. Cl.
USPC ............................... 522/27; 424/400; 528/28

(58) Field of Classification Search
USPC ............................... 424/400; 522/27; 528/28
See application file for complete search history.

(56) References Cited

U.S. PATENT DOCUMENTS

| | | | | |
|---|---|---|---|---|
| 3,562,352 A | * | 2/1971 | Nyilas | ...................... 525/440.04 |
| 4,622,348 A | | 11/1986 | Jacobine et al. | |
| 5,189,217 A | | 2/1993 | Griffiths et al. | |
| 5,221,724 A | | 6/1993 | Li et al. | |

* cited by examiner

*Primary Examiner* — Richard Schnizer
*Assistant Examiner* — Yanzhi Zhang
(74) *Attorney, Agent, or Firm* — Brooks Kushman P.C.

(57) ABSTRACT

Readily emulsifyable silicone copolymers containing urethanesulfonamido linking groups are prepared by reacting a hydroxyl-functional organic polymer with a halo- or pseudohalo-sulfonyl isocyanate, and then reacting the halo- or pseudohalo-sulfonyl product with an organopolysiloxane bearing aminoalkyl groups, preferably in stoichiometric excess.

16 Claims, No Drawings

PROCESS FOR PRODUCING SILOXANE COPOLYMERS WITH URETHANE-SULPHONAMIDO LINKING GROUPS

CROSS-REFERENCE TO RELATED APPLICATIONS

This application is the U.S. national phase of PCT Appln. No. PCT/EP2011/062460 filed Jul. 20, 2011 which claims priority to German application 10 2010 038 487.9 filed Jul. 27, 2010, the disclosures of which are incorporated in their entirety by reference herein.

BACKGROUND OF THE INVENTION

1. Field of the Invention

The invention relates to a process for producing Si—C-linked copolymers from organic polymers and organo-polysiloxanes.

2. Description of the Related Art

SiC-linked copolymers are typically formed from silicones and organic polymers by using essentially three processes: the reaction of silicone polymer such as polyether siloxanes with isocyanates (PU-silicones); the reaction of epoxysiloxanes with polyamines; and the hydrosilylation of allyloxy polymers. While the first two processes require specialty raw materials which are relatively costly, it is costly noble-metal catalysts which are needed in the last case.

U.S. Pat. No. 4,622,348 describes accelerators for free-radically polymerizable compositions obtained via a two-step reaction of chlorosulfonyl isocyanate, by first reacting the isocyanate group with an equivalent amount of a hydroxyl-containing compound and subsequently reacting the sulfonyl chloride group with an equivalent amount of a primary or secondary amine. The hydroxyl-containing compound may be, for example, propargyl alcohol which can be bound to a silicone by a hydrosilylation reaction, or the primary amine may be an aminosilane and a polymer may be obtained by a subsequent condensation polymerization or equilibration.

U.S. Pat. No. 5,189,217 describes a different reactivity pattern for chlorosulfonyl isocyanate in the background art. Chlorosulfonyl isocyanate (CSI) reacts with a methane-sulfonylmethylamine (MMSA) on the sulfone side at first to form a methanesulfonyl-N-methylaminosulfonyl isocyanate (MSMASI). The isocyanate group is then reacted with an amino compound, 2-amino-4,6-dimethoxy-pyrimidine, in a second step.

SUMMARY OF THE INVENTION

The objects of the present invention are to provide a process for producing Si—C-linked copolymers from organic polymers and organopolysiloxanes which does not need costly noble-metal catalysts or specialty raw materials; which proceeds rapidly and to completion even without use of catalysts; which on the basis of freely available foundationstock materials can also be practiced very economically; and with which the copolymers obtained are stable. These and other objects are achieved by a process for producing siloxane polymers having urethanesulfonamido binding groups, by reacting a hydroxyl-functional organic polymer with a halo-sulfonylisocyanate or pseudohalosulfonylisocyanate, is reacted with an amino-functional organopolysiloxanes, preferably in stoichiometric excess of the latter.

DETAILED DESCRIPTION OF THE PREFERRED EMBODIMENTS

The invention thus provides a process for producing siloxane copolymers having urethanesulfonamido binding groups by
a first step of reacting
an organic polymer (1), which has at least one hydroxyl group,
with isocyanate (2) of the formula $$O=C=N-SO_2X \qquad (I)$$

where
X is a halogen atom or a pseudohalogen leaving group, with the proviso that the isocyanate is used in amounts of 0.8 to 1.0 mol, preferably 1.0 mol, of O=C=N— group in (2) per mole of hydroxyl group (—OH) in (1), and a second step of reacting an organic polymer (3), which is obtained from the first step and has at least one group of the formula —O—C(=O)—NH—SO_2X, with an organopolysiloxane (4), which has at least one primary or secondary amino group (—NH—), with the proviso that the organopolysiloxane (4) is used in amounts of 1.0 to 20.0 mol, preferably 1.2 to 10.0 mol, and more preferably 2.0 to 4.0 mol of amino group (—NH—) in (4) per mole of —SO_2X in isocyanate (2).

The process described in U.S. Pat. No. 4,622,348 requires additional auxiliary bases, such as triethylamine, which have to be added in excess. By contrast, the process of the present invention has the advantage that no additional auxiliary bases have to be used. Adding an auxiliary base is only necessary for the range from 1.0 to 2.0 mol of amine group per mole of —SO_2X, although less auxiliary base has to be added.

The invention further provides siloxane copolymers having urethanesulfonamido binding groups between the siloxane polymer and the organic polymer, while the chlorosulfonyl isocyanate adducts obtained as described in U.S. Pat. No. 4,622,348 are not polymers or copolymers but are said to be useful accelerators for free-radically polymerizable compounds.

As the organic polymer (1) which has at least one hydroxyl group, the process of the present invention preferably utilizes a compound of the formula $$Poly(-OH)_r \qquad (II)$$

where
r is an integer from 1 to 10, preferably 1, 2 or 3, more preferably 1 or 2, and
Poly is a mono- to decavalent, preferably mono-, di- or trivalent and more preferably a mono- or divalent organic polymer-derived radical which preferably contains at least one ≡C—O—C≡ or —C(=O)—O—C≡ group and preferably is a polyether radical.

The organic polymer (1) is preferably a compound of the formula $$R^1[(-B)_s-OH]_r \qquad (III)$$

where
B is a radical of the formula —O—(C=O)_p—R^5—,
R^1 is a mono- to decavalent, preferably mono-, di- or trivalent and more preferably a mono- or divalent hydrocarbon radical of 1 to 30 carbon atoms, preferably 1 to 18 carbon atoms,
R^5 is a linear or branched C_2-C_8-alkylene radical,
p is 0 or 1, preferably 0,
s is an integer from 1 to 100, preferably 8 to 60, and r is as defined above.

Examples of monovalent hydrocarbon radicals $R^1$ of 1 to 18 carbon atoms are alkyl radicals such as the methyl, ethyl, n-propyl, isopropyl, 1-n-butyl, 2-n-butyl, isobutyl, tert-butyl, n-pentyl, isopentyl, neopentyl and tert-pentyl radicals, hexyl radical such as the n-hexyl radical, heptyl radical such as the n-heptyl radical, octyl radical such as the n-octyl radical and isooctyl radical such as the 2,2,4-trimethylpentyl radical, nonyl radical such as the n-nonyl radical, decyl radical such as the n-decyl radical, dodecyl radical such as the n-dodecyl radical, and octadecyl radical such as the n-octadecyl radical; cycloalkyl radical such as cyclopentyl, cyclohexyl, cycloheptyl and methylcyclohexyl radicals; alkenyl radical such as the vinyl, 5-hexenyl, cyclohexenyl, 1-propenyl, allyl, 3-butenyl and 4-pentenyl radicals; alkynyl radical such as the ethynyl, propargyl and 1-propynyl radical; aryl radical such as the phenyl, naphthyl, anthryl and phenanthryl radicals; alkaryl radical such as o-, m-, and p-tolyl radicals, xylyl radicals and ethylphenyl radicals; and aralkyl radical such as the benzyl radical, and the α- and the β-phenylethyl radicals.

Examples of divalent radicals $R^1$ are radicals of the formula
—$CH_2CH_2$—
—$CH_2CH(CH_3)$—
—$CH_2CH_2CH_2CH_2$—
—$CH_2CH_2CH_2CH_2CH_2CH_2$—
and examples of tri- and tetravalent radicals $R^1$ are radicals of the formula
—$CH_2(CH—)CH_2$—
$CH_3C(CH_2—)_3$
$C_2H_5C(CH_2—)_3$
$C(CH_2—)_4$ Preferably, B may be considered as a ring-opened epoxide or lactone of 2 to 8, preferably 2 to 6, carbon atoms.

Examples of B are radicals of the formula
—$OCH_2CH_2$—
—$OCH_2CH(CH_3)$—
—$OCH(CH_3)CH_2$—
—$OCH_2CH_2CH_2CH_2$—
—$OCH_2C(CH_3)_2$—
—$O(C=O)$—$CH_2CH_2CH_2$—
—$O(C=O)$—$CH_2CH_2CH_2CH_2$—
—$O(C=O)$—$CH_2CH_2CH_2CH_2CH_2$—

Preference is given to polyether radicals containing from 1 to 100, more preferably from 8 to 60 of groups B. The organic polymer (1) hence contains s×r of these groups.

The organic polymers (1) preferably contain one or more oxyethylene, oxypropylene or oxybutylene units or mixed forms in a block-type or random arrangement. Preference for use as organic polymer (1) is therefore given to polyethers of the formula $$R^6—[O—R^5]_s—O—H \qquad (IV),$$

more preferably those of the formula $$R^6—[O—CH_2—CH(CH_3)]_x—[O—CH_2—CH_2]_y—O—H \qquad (V)$$

where
$R^5$ is as defined above,
$R^6$ is a hydrogen atom, a hydrocarbon radical of 1 to 18 carbon atoms or a radical of the formula $R^7$—C(O)—, where
$R^7$ is a $C_1$-$C_{18}$-alkyl radical,
x is an integer from 0 to 100, and
y is an integer from 0 to 100,
with the proviso that said polymer (1) contains at least one oxyalkylene group.

Preferably, $R^6$ is a hydrogen atom or a hydrocarbon radical of 1 to 8 carbon atoms.

The organic polymers (1) can have either primary, secondary or tertiary carbinol ends. In line with the index "r" they are preferably mono-, di- or tri-functional and more preferably mono- or difunctional. The organic polymers (1) are produced by methods which are common general knowledge.

The X radical in the compound (2) is preferably chlorine. Chlorosulfonyl isocyanate (CSI) is therefore preferred as compound (2).

Examples of pseudohalogen radicals in (2) are those of the formula —OCN, —SCN, —$N_3$.

The first step of the process according to the present invention is preferably performed at 0 to 50° C., more preferably 5 to 30° C., in order that secondary reactions may be avoided. The first step of the process is preferably carried out at the pressure of the ambient atmosphere, i.e., at 1020 hPa, but can also take place at higher or lower pressures.

The reaction in the first step of the process invention can be carried out neat or in solution, in which case the solution has to be anhydrous. Examples of solvents are ethers, glycol ethers, esters or ketones.

The organic polymers (1) which are employed preferably have a low melting point, more preferably a melting point of less than 30° C. and even more preferably of less than 10° C.

The second step of the process preferably comprises metering the organic polymer (3) obtained in the first step, which has at least one group of the formula —O—C(=O)—NH—$SO_2X$, into the organopolysiloxane (4), which has at least one primary or secondary amino group (—NH—).

Preferably, the primary or secondary amino group in (4) is an Si—C-bound group A of the general formula $$—R^2—[NR^3—R^4—]_gNHR^3 \qquad (VI),$$

where
$R^2$ is a divalent linear or branched hydrocarbon radical of 1 to 18 carbon atoms,
$R^3$ is a hydrogen atom or a monovalent hydrocarbon radical of 1 to 18 carbon atoms, preferably a $C_1$-$C_4$-alkyl radical, or an acyl radical, preferably a hydrogen atom,
$R^4$ is a divalent hydrocarbon radical of 1 to 6 carbon atoms, and
g is 0, 1, 2, 3 or 4, preferably 0 or 1.

Preferably, the organopolysiloxanes used as organo-polysiloxanes (4) contain groups of the general formula

$$A_aR_b(R'O)_cSiO_{\frac{4-(a+b+c)}{2}} \qquad (VII)$$

where
A is as defined above,
R is a monovalent hydrocarbon radical with 1 to 18 carbon atoms,
R' is a hydrogen atom or a monovalent hydrocarbon radical having 1 to 18 carbon atoms, preferably a $C_1$-$C_4$-alkyl radical,
a is 0 or 1,
b is 0, 1, 2 or 3,
c is 0 or 1,
with the proviso that the sum a+b+c is ≤3, and in that the organopolysiloxanes contain at least one A radical per molecule.

Preferably, the organopolysiloxanes used as organo-polysiloxanes (4) have the general formula $$A_kR^*_{3-k}SiO(R_2SiO)_m(AR^*SiO)_nSiR^*_{3-k}A_k \qquad (VIII)$$

where
$R^*$ is R or a radical of formula —OR', where R and R' are each as defined above, k is 0 or 1,
m is 0 or an integer from 1 to 1000,
n is 0 or an integer from 1 to 50,
with the proviso that the organopolysiloxanes contain at least one A radical per molecule.

Examples of monovalent hydrocarbon radicals R of 1 to 18 carbon atoms are alkyl radicals, such as the methyl, ethyl, n-propyl, isopropyl, 1-n-butyl, 2-n-butyl, isobutyl, tert-butyl, n-pentyl, isopentyl, neopentyl and tert-pentyl radicals, hexyl radical such as the n-hexyl radical, heptyl radical, such as the n-heptyl radical, octyl radical such as the n-octyl radical and isooctyl radical such as the 2,2,4-trimethylpentyl radical, nonyl radical such as the n-nonyl radical, decyl radical such as the n-decyl radical, dodecyl radical such as the n-dodecyl radical, and octadecyl radical such as the n-octadecyl radical; cycloalkyl radical such as cyclopentyl, cyclohexyl, cycloheptyl and methylcyclohexyl radicals; alkenyl radical such as the vinyl, 5-hexenyl, cyclohexenyl, 1-propenyl, allyl, 3-butenyl and 4-pentenyl radicals; alkynyl radical such as the ethynyl, propargyl and 1-propynyl radicals; aryl radical such as the phenyl, naphthyl, anthryl and phenanthryl radical; alkaryl radicals such as o-, m-, and p-tolyl radicals, xylyl radicals and ethylphenyl radicals; and aralkyl radical such as the benzyl radical, and the α- and the β-phenylethyl radicals.

Preferred examples of A radicals are radicals of the formulae $H_2N(CH_2)_3$—
$H_2N(CH_2)_2NH(CH_2)_3$—
$H_2N(CH_2)_2NH(CH_2)CH(CH_3)CH_2$—
(cyclohexyl)$NH(CH_2)_3$—
$CH_3NH(CH_2)_3$—
$(CH_3)_2N(CH_2)_3$—
$CH_3CH_2NH(CH_2)_3$—
$(CH_3CH_2)_2N(CH_2)_3$—
$CH_3NH(CH_2)_2NH(CH_2)_3$—
$(CH_3)_2N(CH_2)_2NH(CH_2)_3$—
$CH_3CH_2NH(CH_2)_2NH(CH_2)_3$—
$(CH_3CH_2)_2N(CH_2)_2NH(CH_2)_3$— and partially acetylated forms thereof.

Particularly preferred examples of A radicals are radicals of the formulae $H_2N(CH_2)_3$—
$H_2N(CH_2)_2NH(CH_2)_3$—
(cyclohexyl)$NH(CH_2)_3$—
(acetyl)-$NH(CH_2)_2NH(CH_2)_3$—
$H_2N(CH_2)_2N$(acetyl)$(CH_2)_3$—

The radical R* preferably has the meaning of R.

The second step of the process may use organic and inorganic auxiliary bases in order that the resulting acid HX may be neutralized, although this is not preferred. When auxiliary bases are used, they should be as minimally nucleophilic as possible in order that the progress of the reaction may not be impeded.

The organopolysiloxanes (4), in addition to their primary and secondary amino groups, may also contain tertiary amino groups which act as acid-scavengers in the second step of the process and become protonated therein. These are accordingly not added separately as monomeric compounds, but are part of the copolymer and thus also co-determine its physical properties, such as water solubility and self-dispersibility.

The second step of the process is preferably performed at a temperature of 0° to 80° C., more preferably 20° to 50° C., and is preferably carried out at the pressure of the ambient atmosphere, i.e., at about 1020 hPa, but can also be carried out at higher or lower pressures.

The process provides siloxane copolymers having urethanesulfonamido binding groups. The invention accordingly provides siloxane copolymers containing per molecule at least one urethane-sulfonamido binding group selected from the group of formulae (Poly)-O—(C=O)—NH—SO$_2$—NH[—R$^4$—NZ]$_g$—R$^2$—(Si≡)    (IX) and H—NH[—R$^4$—NZ]$_g$—R$^2$—(Si≡)    (IX')

and their mixtures (IX) and (IX'),
where
Z is a radical of the formula —SO$_2$—NH—(C=O)—O-(Poly) or is an R$^3$ radical, where when Z is an R$^3$ radical, the N-atom is protonated,
R$^2$, R$^3$ and R$^4$ are each as defined above,
(Si≡) is a link to the organopolysiloxane via an Si—C bond, and
(Poly) is a link to an organic polymer-derived radical.

The siloxane copolymers of the present invention preferably contain urethanesulfonamido binding groups of formula (IX) and/or (IX') in amounts from 0.2 to 10 wt %, more preferably from 0.5 to 5 wt % and most preferably in amounts of from 0.5 to 2.0 wt %, based on the total weight of siloxane copolymers.

The siloxane copolymers of the present invention differ in principle from the chlorosulfonyl isocyanate adducts described in U.S. Pat. No. 4,622,348, which are used as accelerators for free-radically polymerizable compounds, in the very much smaller amount of urethane-sulfonamido binding groups.

This results in different properties/advantages on the part of the siloxane copolymers of the present invention, such as these compounds being liquid and hence easier to process. The sulfur content is preferably less than 2 wt % and more preferably far less than 1 wt %.

The organic polymers (3) obtained after the first step of the process, which have groups of the formula —O—C(=O)—NH—SO$_2$X, contain sulfonyl groups which, in the second step of the process, react equally with the primary and the secondary amino groups in the organo-polysiloxanes (4), essentially on a statistical basis. The unsulfonated amino groups are preferably protonated by the resulting acid HX and are then in the form of an ammonium group.

The siloxane copolymers of the present invention, in addition to the urethanesulfonamido binding groups, therefore preferably comprise per molecule at least one Si—C-bound ammonium group A' of the formula —R$^2$—[N$^{(+)}$HR$^3$—R$^4$—]$_g$N$^{(+)}$H$_2$R$^3$ 2*X$^{(-)}$    (X)

where
R$^2$, R$^3$, R$^4$, X and g are each as defined above.

Preferred urethanesulfonamido binding groups result from the use of preferred amino radicals of the formula H$_2$N—(CH$_2$)$_3$— and H$_2$N—(CH$_2$)$_2$—HN—(CH$_2$)$_3$— and therefore are those of the formula (Poly)-O—(C=O)—NH—SO$_2$—NH—(CH$_2$)$_3$—(Si≡)

(Poly)-O—(C=O)—NH—SO$_2$—NH—(CH$_2$)$_2$—$\overset{+}{N}H_2$—(CH$_2$)$_3$—(Si≡) * X$^-$ (Poly)-O—(C=O)—NH—SO$_2$—NH—(CH$_2$)$_2$—$\underset{|}{\overset{Z}{N}}$—(CH$_2$)$_3$—(Si≡), where Z, (Si≡) and (Poly) are each as defined above.

Preferably, the urethanesulfonamido binding group is bound to the organopolysiloxane via a siloxane unit of the formula —SiR*$_d$O$_{(3-d)/2}$, where d is 0, 1 or 2, preferably 1 or 2, and R* is as defined above.

Preferably, the organic polymer-derived radical (Poly), to which the urethanesulfonamido binding group is bound, is a polyether group of the formula $-(O-R^5)_s-$, preferably of the formula $-[O-CH_2-CH(CH_3)]_x-[O-CH_2-CH_2]_y-$, where $R^5$, s, x and y are each as defined above.

This urethanesulfonamido binding group is highly polar and develops strong hydrogen bond interactions. It can therefore be advantageous to add viscosity modifiers to the reaction products, if readily flowable copolymers are desired. It may be preferable to add carbinols, more preferably the low molecular weight alcohols such as MeOH, EtOH, PrOH, i-PrOH, n-BuOH, i-BuOH, and also the lower alkoxylates thereof.

Molecular weights ($M_n$) of siloxane copolymers of the present invention are preferably in the range of from 5000 to 1,000,000 daltons, more preferably in the range from 10,000 to 200,000 daltons. A general assignment of viscosity parameters to $M_n$ is not possible, since viscosity is greatly dependent on which organic polymers (3) and organopolysiloxanes (4) are used, especially on the number of OH groups in (3) and of amino groups (—NH—) in (4), and hence also on the density of urethanesulfonamido binding groups between the organic polymer and the organopolysiloxane in the siloxane copolymer.

The invention further provides emulsions containing
(i) inventive siloxane copolymers with urethane-sulfonamido binding groups
(ii) optionally emulsifiers, and
(iii) water.

The emulsions of the present invention are produced by mixing components (i), (ii) and (iii), preferably intensively.

Technologies for producing emulsions of organo-polysiloxanes are known. The intensive mixing can be effected in rotor-stator stirring apparatus, colloid mills or in high-pressure homogenizers.

The amount of water utilized in the emulsions of the present invention is preferably in the range of from 80 to 1000 parts by weight and more preferably in the range of 100 to 500 parts by weight, all based on 100 parts by weight of siloxane copolymers (i) according to the present invention.

Emulsifiers (ii) can be any cationic, anionic or nonionic emulsifiers not only individually but also as mixtures of various emulsifiers which are useful in preparing aqueous emulsions of organopolysiloxanes.

When emulsifiers are optionally used in emulsions of the present invention they are preferably used in amounts of from 5 to 40 parts by weight and more preferably 5 to 20 parts by weight, all based on 100 parts by weight of siloxane copolymers (i).

The siloxane copolymers of the present invention can be varied via the choice of stoichiometry as being water-soluble or as being self-emulsifying (so-called self-emulsifying systems), i.e., they require no further auxiliaries for emulsification. The siloxane copolymers can be used for treating textile fabrics, textile fibers and leather, as additives in coatings and paints, as ingredients in cosmetic formulations and as surface-active agents. They have more particularly outstanding properties as textile softeners.

EXAMPLE 1

340 g of a dried random copolymer formed from equimolar amounts of ethylene oxide and propylene oxide and having an OH number of 44.3 ($M_n$=2530; an OH number of 56.1 is to be understood as meaning 1 milliequivalent of OH/g of polyether, i.e., OH number 44.3 is 0.79 milliequivalent of OH/g of polyether) are initially charged under a protective gas ($N_2$) and reacted with 38.0 g of chlorosulfonyl isocyanate while cooling. The —OH/—NCO ratio is 1.00. The spontaneous exothermic reaction ends on completing the metered addition of chlorosulfonyl isocyanate. The acid number of the yellowish clear product is 80.82 (mg KOH/g). $^1$H NMR shows complete conversion of carbinol groups to chloro-sulfonylurethane ($-O_2CNHSO_2Cl$) groups.

42.7 g of this polyether with chlorosulfonylurethane end groups are metered in about 20 minutes into 100.0 g of an α,ω-aminoethylaminopropylpolydimethylsiloxane (diluted with 35.7 g of isopropanol) having an amine number of 0.758. The —NH—/—$SO_2$Cl mole ratio is 2.50. The spontaneously ensuing exothermic reaction causes the internal temperature to rise by 9° K., while there is also a strong increase in viscosity. The initially cloudy reaction mixture turns into a highly viscous clear solution of the polyether-siloxane copolymer in isopropanol (80% strength). The copolymer contains around 11 wt % of EO groups and 15 wt % of PO groups. The proportion of amino groups in the siloxane raw material which react is 80% in that equimolar portions (40%) are protonated (by the freed acid HCl) and form the sulfonamide. The $^1$H NMR show the decrease in the N—$CH_2$— groups of the starting material at between 2.3 and 2.7 ppm to 20% of its original value.

50 g of the product solution are diluted with 30 g of isopropanol to a 50% strength solution for greater simplicity of handling. To produce a copolymer emulsion, a total of 53 g of demineralized water are added by hand with a spatula a little at a time while stirring. This gives a very finely divided emulsion which contains 30% of the polyether-siloxane copolymer (pH=5). This emulsion is unchanged after one week at room temperature, as is its dilution to a 2% copolymer content.

EXAMPLE 2

Example 1 is repeated except that only 26.7 g of the chlorosulfonylurethane polyether are added to the 100 g of aminosiloxane (diluted with 31.7 g of isopropanol). These starting quantities amount to an —NH—/—$SO_2$Cl ratio of 4.00. The spontaneous exothermic reaction causes the temperature to increase by 5° K. together with an appreciable increase in viscosity. A clear 80% strength solution is obtained of a polyether-siloxane copolymer containing around 8 wt % of EO groups and 11 wt % of PO groups. The amino groups of the siloxane were 50% converted with 25% of sulfamide groups and 25% of ammonium chloride groups being formed. The $^1$H NMR indicates the reduction in N—$CH_2$ groups of the amino-siloxane (2.3-2.7 ppm) to 50% of its original value.

In the same way as in Example 1, 80 g of a 50% strength solution in isopropanol can be converted into a stable finely divided emulsion (pH=7) by portionwise addition of 53 g of water.

EXAMPLE 3

Slow metered addition of 31.3 g of chlorosulfonyl isocyanate with cooling converts 400 g of a dried random allyloxy-ethoxylate-co-propoxylate (equimolar) having an OH number of 31.0 into 431.3 g of an allyl polyether chlorosulfonylurethane. The acid number is 56.92.

29.6 g of this allyl polyether derivative are reacted with 100 g of a customary aminosiloxane consisting of aminoethylaminopropylmethylsiloxy and dimethylsiloxy units and MeO/HO end groups (Me=methyl radical) having an amine number of 0.305 and a viscosity of 1220 mm²/s (25° C.) by adding the chlorosulfonylurethane polyether in 20 minutes to a solution of the amino-siloxane in 32.4 g of isopropanol. The —NH—/—SO₂Cl mol ratio is 2.00. The reaction mixture heats up by about 5° K., which is associated with an appreciable increase in viscosity. The initially very cloudy reaction mixture gives a clear 80% strength solution of a poly-ether-siloxane copolymer which contains about 9 wt % of EO groups and 13 wt % of PO groups. The amino groups of the siloxane were completely converted into 50% of sulfamide groups and 50% of ammonium chloride groups, which is evident in the ¹H NMR by the absence of signals for the N—CH₂ groups (2.3-2.7 ppm).

A 50 g quantity of this copolymer solution is admixed with 7.1 g of isopropanol to produce a 70% strength solution. By stirring altogether 76.2 g of demineralized water in a little at a time, a very finely divided stable emulsion is obtained.

EXAMPLE 4

100 g of the aminosiloxane of Example 1 are diluted with 40.9 g of isopropanol. A mixture of 26.7 g of the chlorosulfonylurethane polyether from Example 1 and 36.9 g of the chlorosulfonylurethane polyether from Example 3 is added at room temperature. The —NH—/—SO₂Cl use ratio is 2.00. During the metered addition of 30 minutes, the internal temperature rises by about 8° K., with a distinctly apparent increase in viscosity. This gives an 80% strength emulsion of the polyether-siloxane copolymer in isopropanol, which contains around 15 wt % of EO groups and 20 wt % of PO groups. The amino groups of the siloxane have been completely converted into 50% of sulfamide groups and 50% of ammonium chloride groups, which corresponds to an amine number of 0.23 for the copolymer.

The reaction product is further diluted with isopropanol to 50%. By stirring altogether 53 g of water into 80 g of this solution a little at a time, a very finely divided emulsion having a 30 wt % copolymer content is readily obtained.

What is claimed is:

1. A process for producing siloxane copolymers having urethanesulfonamido groups, comprising:
    reacting in a first step,
    an organic polymer (1), which has at least one hydroxyl group,
    with an isocyanate (2) of the formula (I)

$$O=C=N-SO_2X \qquad (I)$$

wherein
    X is a halogen atom or a pseudohalogen radical,
    with the proviso that the isocyanate is used in an amount of 0.8 to 1.0 mol of O=C=N— groups per mole of hydroxyl group (—OH) in (1), and
    reacting, in a second step
    an organic polymer (3), which is obtained from the first step and has at least one group of the formula —O—C(=O)—NH—SO₂X, with an organopolysiloxane (4), which has at least one primary or secondary amino group (—NH—),
    with the proviso that the organopolysiloxane (4) is used in amounts of 1.2 to 4.0 mol of amino group (—NH—) per mole of —SO₂X in isocyanate (2).

2. The process of claim 1, wherein the isocyanate is used in an amount of 1.0 mol of O=C=N— group per mol of hydroxyl group in (1).

3. The process of claim 1, wherein the organopolysiloxane (4) is used in an amount to supply 2.0 to 4.0 mol of amino groups per mol of —SO₂X groups in isocyanate (2).

4. The process of claim 2, wherein the organopolysiloxane (4) is used in an amount to supply 2.0 to 4.0 mol of amino groups per mol of —SO₂X groups in isocyanate (2).

5. The process of claim 1, wherein the organic polymer (1) has the formula (III)

$$R^1[(-B)_s-OH]_r \qquad (III)$$

wherein
    B is a radical of the formula —O—(C=O)$_p$—R⁵—,
    R¹ is a hydrocarbon radical of 1 to 30 carbon atoms,
    R⁵ is a linear or branched C₂-C₈-alkylene radical,
    p is 0 or 1,
    r is an integer from 1 to 10, and
    s is an integer from 1 to 100.

6. The process of claim 5, wherein R¹ is mono-, di-, or trivalent.

7. The process of claim 5, wherein R¹ contains from 1 to 18 carbon atoms.

8. The process of claim 5, wherein p is 0.

9. The process of claim 1, wherein the organic polymer (1) is a polyether of the formula (V)

$$R^6-[O-CH_2-CH(CH_3)]_x-[O-CH_2-CH_2]_y-O-H \qquad (V)$$

wherein
    R⁶ is a hydrogen atom, a hydrocarbon radical of 1 to 18 carbon atoms or a radical of the formula R⁷—C(O)—,
    R⁷ is a C₁-C₁₈-alkyl radical,
    x is an integer from 0 to 100, and
    y is an integer from 0 to 100,
with the proviso that the polymer (1) contains at least one oxyalkylene group.

10. The process of claim 1, wherein the organopolysiloxane (4) comprises units of the formula (VII)

$$A_aR_b(R'O)_cSiO_{\frac{4-(a+b+c)}{2}} \qquad (VII)$$

wherein
    A is an Si—C-bound radical of the formula (VI)

$$-R^2-[NR^3-R^4-]_gNHR^3 \qquad (VI),$$

R is a monovalent hydrocarbon radical having 1 to 18 carbon atoms,
    R' is a hydrogen atom or a monovalent hydrocarbon radical having 1 to 18 carbon atoms, R² is a divalent linear or branched hydrocarbon radical having 1 to 18 carbon atoms,
    R³ is hydrogen or a hydrocarbon radical having 1 to 18 carbon atoms, or acyl radical,
    R⁴ is a divalent hydrocarbon radical having 1 to 6 carbon atoms,
    a is 0 or 1,
    b is 0, 1, 2 or 3,
    c is 0 or 1,
    g is 0, 1, 2, 3 or 4,
with the proviso that the sum a+b+c is ≤3, and in that the organopolysiloxane contains at least one A radical per molecule.

11. The process of claim 1, wherein an organopolysiloxane (4) has the formula (VIII)

$$A_kR^*_{3-k}SiO(R_2SiO)_m(AR^*SiO)_nSiR^*_{3-k}A_k \qquad (VIII)$$

wherein
R* is R or a radical of formula —OR',
R is a monovalent hydrocarbon radical having 1 to 18 carbon atoms,
R' is hydrogen or a hydrocarbon radical having 1 to 18 carbon atoms,
k is 0 or 1,
m is 0 or an integer from 1 to 1000,
n is 0 or an integer from 1 to 50,
A is a radical of the formula (VI)

$$—R^2—[NR^3—R^4—]_g NHR^3 \quad (VI),$$

wherein $R^2$ is bonded to a silicon atom of organopolysiloxane (4)
g is 1, 2, 3, or 4,
$R^2$ is a divalent linear or branched hydrocarbon radical having 1 to 18 carbon atoms,
$R^3$ is hydrogen or a monovalent hydrocarbon radical having 1 to 18 carbon atoms, or an acyl radical,
$R^4$ is a divalent hydrocarbon radical having 1 to 6 carbon atoms,
with the proviso that the at least one organopolysiloxane contains at least one A radical per molecule.

12. A siloxane copolymer containing per molecule at least one urethanesulfonamido group of the formulae (IX) and/or (IX')

$$(Poly)-O—(C=O)—NH—SO_2—NH[—R^4—NZ]_g—R^2—(Si\!\equiv\!) \quad (IX)$$

$$H—NH[—R^4—NZ]_g—R^2—(Si\!\equiv\!) \quad (IX')$$

wherein
Z is a radical of the formula —$SO_2$—NH—(C=O)—O-(Poly) or is an $R^3$ radical, where when Z is an $R^3$ radical, the N-atom is protonated,
$R^2$ is a divalent linear or branched hydrocarbon radical having 1 to 18 carbon atoms,
$R^3$ is hydrogen or a monovalent hydrocarbon radical having 1 to 18 carbon atoms, or an acyl radical,
$R^4$ is a divalent hydrocarbon radical having 1 to 6 carbon atoms,
(Si≡) is a link to an organopolysiloxane via an Si—C bond, and
(Poly) is a link to an organic polymer radical.

13. The siloxane copolymer of claim 12, which contains from 0.2 to 10 wt % of urethanesulfonamido groups of formulae (IX) and/or (IX'), based on the total weight of siloxane copolymer.

14. The siloxane copolymer of claim 12, wherein in addition to the urethanesulfonamido groups of formulae (IX) and/or (IX') the siloxane copolymer contains at least one ammonium group of the formula (X)

$$—R^2—[N^{(+)}HR^3—R^4—]_g N^{(+)}H_2 R^3 \; 2{\ast}X^{(-)} \quad (X)$$

wherein
$R^2$ is a divalent linear or branched hydrocarbon radical having 1 to 18 carbon atoms bonded to silicon by an Si—C bound,
$R^3$ is hydrogen or a monovalent hydrocarbon radical having 1 to 18 carbon atoms, or an acyl radical,
$R^4$ is a divalent hydrocarbon radical having 1 to 6 carbon atoms, and
X is a halogen atom or a pseudohalogen radical.

15. An emulsion containing
(i) at least one siloxane copolymer having urethanesulfonamido groups of claim 12,
(ii) optionally, one or more emulsifiers, and
(iii) water.

16. An emulsion containing
(i) at least one siloxane copolymer having urethanesulfonamido groups prepared by the process of claim 1,
(ii) optionally, one or more emulsifiers, and
(iii) water.

* * * * *